United States Patent [19]
Browne

[11] Patent Number: 5,921,891
[45] Date of Patent: Jul. 13, 1999

[54] ADAPTIVE INTERACTIVE EXERCISE SYSTEM

[75] Inventor: James Neville Browne, Woollahra, Australia

[73] Assignee: Hayle Brainpower Pty. Ltd., Wollahra, Australia

[21] Appl. No.: 08/913,173

[22] PCT Filed: Feb. 21, 1996

[86] PCT No.: PCT/AU96/00091
 § 371 Date: Sep. 25, 1997
 § 102(e) Date: Sep. 25, 1997

[87] PCT Pub. No.: WO96/26495
 PCT Pub. Date: Aug. 29, 1996

[30]   Foreign Application Priority Data

Feb. 21, 1995 [AU] Australia ................................ PN1271

[51] Int. Cl.[6] .................................................. A63B 21/00
[52] U.S. Cl. ...................... 482/8; 482/1; 482/4; 482/901
[58] Field of Search ................................. 482/1–9, 51, 54, 482/900–902

[56]         References Cited

U.S. PATENT DOCUMENTS

| 4,686,624 | 8/1987 | Blum et al. . | |
|---|---|---|---|
| 5,213,555 | 5/1993 | Hood et al. | 482/57 |
| 5,466,200 | 11/1995 | Ulrich et al. | 482/4 |

FOREIGN PATENT DOCUMENTS

| 33968/93 | 9/1993 | Australia . |
| 0 057 609 | 8/1982 | European Pat. Off. . |
| 0 650 695 A2 | 8/1987 | European Pat. Off. . |
| WO 87/05727 | 9/1987 | WIPO . |
| WO 94/02904 | 3/1994 | WIPO . |

OTHER PUBLICATIONS

Derwent Abstract, Accession No. 94–164905/20 Class P31, SU 1799545, A(ALTAI MED INST) Mar. 7, 1993.

*Primary Examiner*—Glenn E. Richman
*Attorney, Agent, or Firm*—Darby & Darby

[57]              ABSTRACT

An improved user monitor 102 is a component of the illustrated monitoring system. This system includes a master data processor in the form of a computer 101 arranged to store physical parameter data for a plurality of users. Each user is provided with a user monitor 102 which is arranged to monitor at least one physical parameter of the user during exercise and store data relating to the physical parameter. This data can subsequently be transmitted to the master data processor by pulse transmission from the user monitor down a telephone line 103. The master data processor then compares the received data with the stored data for the user in order to enable monitoring of the progress of the user in an exercise regimen which has been preset for him.

At the end of each exercise, the exercise monitor screen shows an effort rating of "EFFORT 12".

The client can alter the number anywhere from 6 to 20 by using the keypad 14 on the face of the exercise monitor. The number entered relates to the client's perception of the degree of difficulty experienced during the exercise, for example, 9 is very light, 11 is "fairly light", 14 is "somewhat hard", and 15 is "hard". If a certain undesirable pattern of Effort Rating is detected the monitor is programmed to automatically respond to the undesirable pattern and to slowly alter the prescription.

28 Claims, 6 Drawing Sheets

ADAPTIVE INTERACTIVE EXERCISE SYSTEM

INTRODUCTION

The present invention relates to a system for the provision of an exercise regimen for users and particularly to a system which facilitates semi-automated monitoring of a user's progress in the exercise regimen. In particular, the present invention provides an improvement to a device for monitoring heartbeat which forms a component of such a system.

BACKGROUND OF THE INVENTION

One of the most important factors in maintaining good health is physical exercise. A number of major studies in recent years have demonstrated the health benefits of regular physical exercise, particularly in respect to maintaining a healthy cardiovascular system.

The present inventor is also named as the inventor in commonly assigned PCT Application No PCT/AU93/00367 directed to an exercise system which is incorporated herein by reference.

This prior application describes a fitness monitoring system comprising a personal exercise monitoring device preprogrammed with data to guide the user in a desirable exercise regime, the monitoring device including communication means enabling connection to a central computer system for downloading data recorded during an exercise session to the central computer. The central computer has stored information enabling it to rate the user's performance and provide performance reports which enable feedback to the user via a personal trainer.

However, a problem has been found with this prior art system in that when a client reaches their final exercise prescription, it is sometimes found that the final prescription is incorrect and that a slight increase or decrease in exercise heart rate is required to achieve the optimum exercise prescription for that client. It is also sometimes found that the client is not able to keep up with the programmed rate of progression to the final prescription and that an adjustment to the programme is required. However. when clients are asked to alter their exercise prescription they feel that they have failed in some way, whereas in truth the original assessment process simply failed to predict the correct final prescription with sufficient accuracy.

This problem is addressed with an improvement to the exercise monitor, whereby the concept of final prescription has been abandoned and continual user feedback is used to adjust the prescription gradually such that the user always approaches a final heart rate band from below. Once in this final band, the prescription will tend to remain within the band over time depending upon various factors affecting the client.

SUMMARY OF THE INVENTION

The present invention consists in an exercise monitor for facilitating monitoring of the progress of a user in an exercise regime, the exercise monitor being arranged to monitor a user exercise event and to store parameter values relating to the exercise event and including physical parameter measurement means arranged to measure physical parameter data during an exercise event, preset value storage means arranged to store preset values for the physical parameter, comparison means arranged to compare the preset value with the measured physical parameter data, indicator means arranged to indicate when the physical parameter data differs from the preset value by an amount greater than an allowable tolerance, to indicate to the user a required change in exercise intensity, exercise intensity input means arranged to enable input of data indicative of difficulty of a completed exercise, and preset value adjustment means arranged to enable alteration of the preset values in the preset value storage means in response to inputs operable by user.

In a preferred embodiment, the indicator means are arranged to display a preferred effort rating at the end of each exercise. The client can then alter the rating displayed to indicate the client's perception of the degree of difficulty experienced during the exercise by incrementing the rating up or down using buttons on the monitor face. In the preferred embodiment, the optimum index value is 12 while 9 is very light. 11 is "fairly light", 14 is "somewhat hard", and 15 is "hard". This gives the ability to remotely fine tune the Exercise Prescription in response to a certain pattern of Effort Rating. In order to perform the adjustment the monitor device is programmed to automatically respond to the pattern of effort rating values to alter the prescription. Alternatively, if the personal trainer is concerned about the progress of the client, the VoiceMail can be used to instruct the client change their monitor.

The exercise regimen may be any physical exercise routine or system determined for the physical exercise of the user. A user exercise event would generally be a single performance of an exercise routine by the user. For example, the exercise regimen may require the user to undertake a "whole of body" exercise, such as swimming or walking, for example, for a predetermined time period.

The regimen may require that this exercise event be performed a number of times a week.

The user monitor is preferably arranged, during operation, to monitor and store the physical parameter value relating to the user exercise event. The physical parameter value can then be subsequently downloaded to the master data processor means at the user's convenience.

Preferably, during the performance of an exercise event, the user is required to monitor at least one physical parameter with the assistance of the user monitor. The user is preferably required, during the performance of the exercise event, to control his exercising to maintain the physical parameter as close as possible to preset values of the parameter. The preset values for the physical parameter are preferably initially determined for the user before he commences the particular exercise regimen.

In the preferred embodiment of the present invention, physical parameter values stored in the user monitor relate to the heart-rate of the user, and are preferably a measure of heart-rate over a period of time during exercise. Heart rate over the exercise period is a convenient way of monitoring the effect of exercise on the user, and the user's progress in the exercise regimen. It is possible that other physical parameters could be used in the present invention to monitor the user's progress, instead of or in addition to monitoring of heart-rate.

Where heart-rate is used to monitor the user's exercise, the physical parameter values stored are preferably stored in the form of a "heart-rate curve", i.e. a curve plotting heart-rate against time during the period of a single exercise event. When the user first commences the exercise regimen, physiological tests are made on him. From the test results, the master data processing means produces a "heart-rate curve" specific to the particular user. The user heart-rate curve is designed to be "ideal" for the user and his particular exercise event, and during subsequent exercise events (which the user may perform anywhere—in his home, for example) the user is asked to keep his heart-rate as close as possible to this heart-rate curve.

During exercise, the user is required to maintain the particular physical parameter as close as possible to these values. The user monitor is preferably arranged to assist the user in monitoring the physical parameter during exercise, and preferably includes storage means for storing preset values corresponding to values stored in the master data processing means for the physical parameter.

The user monitor further preferably includes memory means for storing values of the physical parameter taken during the performance of the exercise event by the user.

In the preferred embodiment, the physical parameter used is heart-rate.

The user monitor preferably includes means for monitoring the heart-rate of the user during an exercise event and means for storing values of heart-rate at time intervals during the exercise event.

The user monitor preferably further includes means for downloading the stored data relating to an exercise event to the master data processing means. Preferably, the means for downloading comprises means for interfacing with a standard telephone set to send information down a telephone line to the master data processing means.

The user monitor preferably further includes means for storing heart-rate data to enable generation of a "heart-rate curve", i.e. a curve plotting heart-rate against time during the period of a single exercise event, and means for comparing the heart-rate of the user during the exercise event with the generated heart-rate curve, to determine whether or not the user's heart-rate is within predetermined limits of the heart-rate curve. The "heart-rate curve" reflects variations in the user's heart-rate over the period of time of a user exercise event. It is preferably stored in the master data processing means and the user monitor. It may be stored as a plurality of heart-rate readings for predetermined time intervals during the exercise event, rather than actually being in the form of an analogue curve. The curve may be extrapolated from the stored data.

The user monitor is also preferably arranged to store information identifying the date and time of an exercise event. This may be associated with the physical parameter data for the particular exercise event, as a form of "tag" to enable the master data processor to place in time the data from the user monitor. Preferably the user monitor does not store an absolute date and time but rather it counts the time from an exercise event to the point when that event is reported to the central system. This enables the central system to relate the exercise event to a standardised time reference, which is required to take into account time zones and time changes. The user monitor also preferably stores data enabling identification of the user by the master data processing means.

The user monitor is also preferably provided with a logging mode for recording a physical parameter over an extended period of time, the parameter being stored at regular intervals the period of which may vary over the length of the logging period.

The present invention advantageously enables careful monitoring of an exercise programme of a user, without the need for the user to make frequent attendance at a particular location, such as a gymnasium.

BRIEF DESCRIPTION OF THE DRAWINGS

Features and advantages of the present invention will become apparent from the following description of an embodiment thereof, by way of example only, with reference to the accompanying drawings, in which.

DETAILED DESCRIPTION OF THE PREFERRED EMBODIMENT

Figure 5:
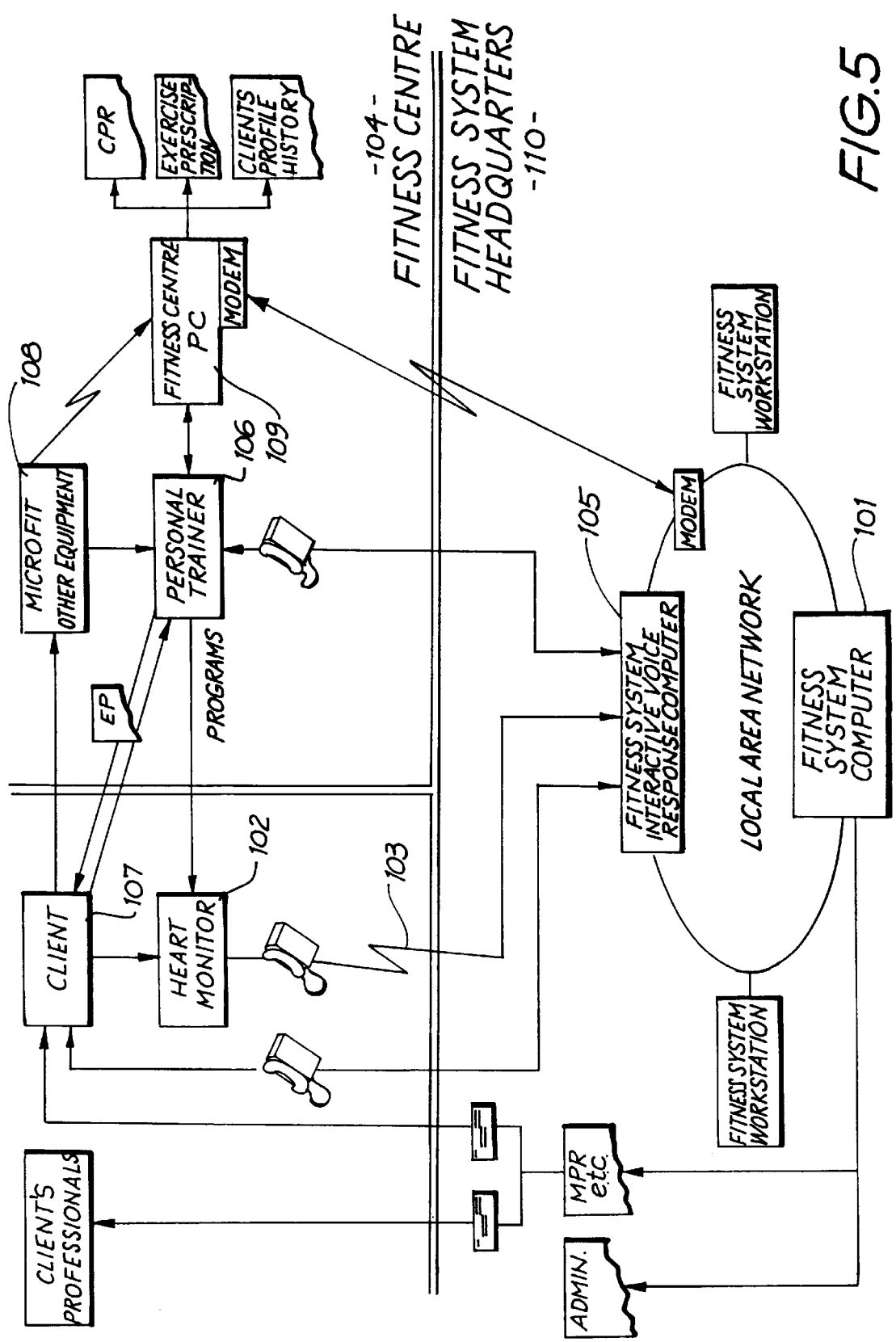
FIG. 5 is an overall block diagram of the preferred embodiment of a system for monitoring training in accordance with the present invention.

Referring to FIG. 5, the preferred embodiment of the present invention is an improved user monitor 102 which is a component of the illustrated monitoring system. This system includes a master data processor in the form of a computer 101 arranged to store physical parameter data for a plurality of users. Each user is provided with a user monitor 102 which is arranged to monitor at least one physical parameter of the user during exercise and store data relating to the physical parameter. This data can subsequently be transmitted to the master data processor by pulse transmission from the user monitor down a telephone line 103. The master data processor then compares the received data with the stored data for the user in order to enable monitoring of the progress of the user in an exercise regimen which has been preset for him.

Previously, the prescription had two phases of activity, the first known as the training phase and the second known as the maintenance phase. At the commencement of the training phase, the client may start exercising with a program comprising a 5 minute warm up, a 5 minute plateau and a 5 minute cool down, with a heart rate during the plateau which may, for example, be in the order of 62% of the client's estimated preferred final aerobic heart rate. The preferred aerobic heart rate is in the range between the aerobic and anaerobic thresholds and represents a target maximum heart rate for exercise.

This rate will be referred to as the metobic heart rate hereinafter. The client's program would then call for him to ramp up his plateau period and heart rate over a period of time until the plateau had a duration of 25 minutes and his heart rate during the plateau period was 90% of the estimated long term maximum metobic heart rate, at which time the training phase would be completed and the client would graduate to the maintenance phase.

In the maintenance phase the client would continue the exercise program comprising 5 minutes warm up, 25 minutes plateau and 5 minutes cool down, but the heart rate maintained during the plateau period would gradually ramp up from 90% of the estimated final metobic heart rate to 100% of that value. This progression is illustrated as curve 2 in FIG. 6.

In the previous system a problem has been noted with some clients where it has been noted that they are exercising at a level considered to be a little more intense than is desirable, indicating either that the programmed rate of progression or original estimate of their final metobic rate was incorrect. When the error in the original prescription resulted in a programme that was too strenuous and the client was asked to adjust their final metobic rate down to the correct Level the client would develop a sense of failure. They would not accept that the original prediction was wrong. They would instead think that they were not up to the expectations of the original assessment. This was a misconception on the part of the client, as prediction is more art than science, but resulted in the client feeling inadequate. With the present improved embodiment of the exercise monitor the adjustment to the prescription can be made quietly without the client being aware that it is taking place. This embodiment no longer employs the concept of the "ideal", Final Prescription or HeartPrint or "ideal" rate of progression. Instead, the correct HeartPrint is the HeartPrint which the user monitor says is correct for that user at that time. It will move up and down under the influence of an Effort Rating input and the exercise history. If the client stops exercising for a few weeks, the user monitor will start the client at a less intense HeartPrint upon recommencing exercise and build the client back up again to their previous level, driven by exercise pattern and Effort Rate pattern. However, the corrections made to the prescription by the monitor must be monitored and in some cases moderated by the personal trainer. For example, if the user consistently reports a high effort rating when exercising a long way below the pre-set level, the monitor will not progress the case further. Trainer intervention is then required and the trainer will be prompted by the central system.

The correction of the prescription or HeartPrint is achieved by using an Exercise Prescription Adjustment. This is a new and improved feature of the exercise monitor. At the end of each exercise, the exercise monitor screen shows an effort rating of "EFFORT 12".

The client can alter the number anywhere from 6 to 20 by using the keypad 14 on the face of the exercise monitor. The number entered relates to the client's perception of the degree of difficulty experienced during the exercise, for example, 9 is very light, 11 is "fairly light", 14 is "somewhat hard", and 15 is "hard". This table of perceived exertion was designed and researched in the U.S. by Professor Borg and it has wide acceptance in the scientific world. It is desirable for clients to work at around 12 Effort Rating and it is now possible to monitor how well the Exercise Prescription was originally designed. This gives the ability to automatically fine tune the Exercise Prescription. If a certain undesirable pattern of Effort Rating is detected the preferred embodiment of the monitor is programmed to automatically respond to the undesirable pattern and to slowly alter the prescription. Alternatively, if the trainer is concerned about the Effort Rating pattern, the client may be requested, via voice mail, to change their exercise pattern or the parameters stored in their exercise monitor or they may be given advice on exercise techniques etc, to correct this problem.

Using the Borg rating as a feedback mechanism, the prescription may be continually adjusted to ensure that the client progresses at an optimum or near optimum rate for the level of commitment and physical condition of the client. With this arrangement, the rate of progression of the client in the training phase will be adjusted in response to three factors as follows:
1. A personalised acceleration rate determined from the medical history and physical examination of the client.
2. Ongoing exercise history of the client.
3. The history of Borg feedback ratings.
4. A personalizable oscillation factor.
5. A personalizable lag/acceleration factor.

The personalised acceleration rate is used to set the basic slope of the initial prescription, and takes into account the initial fitness level and medical history of the client. For example, a client who had undergone a heart operation would have a slower acceleration rate.

The ongoing exercise history of the client takes into account differences between the proposed repetition rate of the exercise sessions and the actual number of exercise sessions accomplished. If the prescription is based upon the client exercising once per day, five days per week, and in practice exercise is only performed on four days of each week then the rate of progression might be decreased to four fifths of the original prescription.

The Borg feedback rating, as explained previously, provides an indication of the client's perception of the difficulty of the exercise session.

This feedback mechanism is used to ensure that the client is not under or over exercising relative to their current level of fitness.

The oscillation factor "filters out" short term variations in the response which would otherwise occur as a result of day to day variations in the performance of the user.

The lag/acceleration factor is used to adjust the intensity of the response (once a response is triggered) to Effort Rating data.

In future embodiments other lifestyle parameters will be collected, such as sleep, stress etc, and used to modify the rate of progression, primarily through modification of the lag/acceleration factor. These lifestyle parameters may also be used to formulate changes to the exercise increment, in combination with other data to propose lifestyle changes and to assist in the monitoring of the effectiveness of recommendations.

Figure 6:
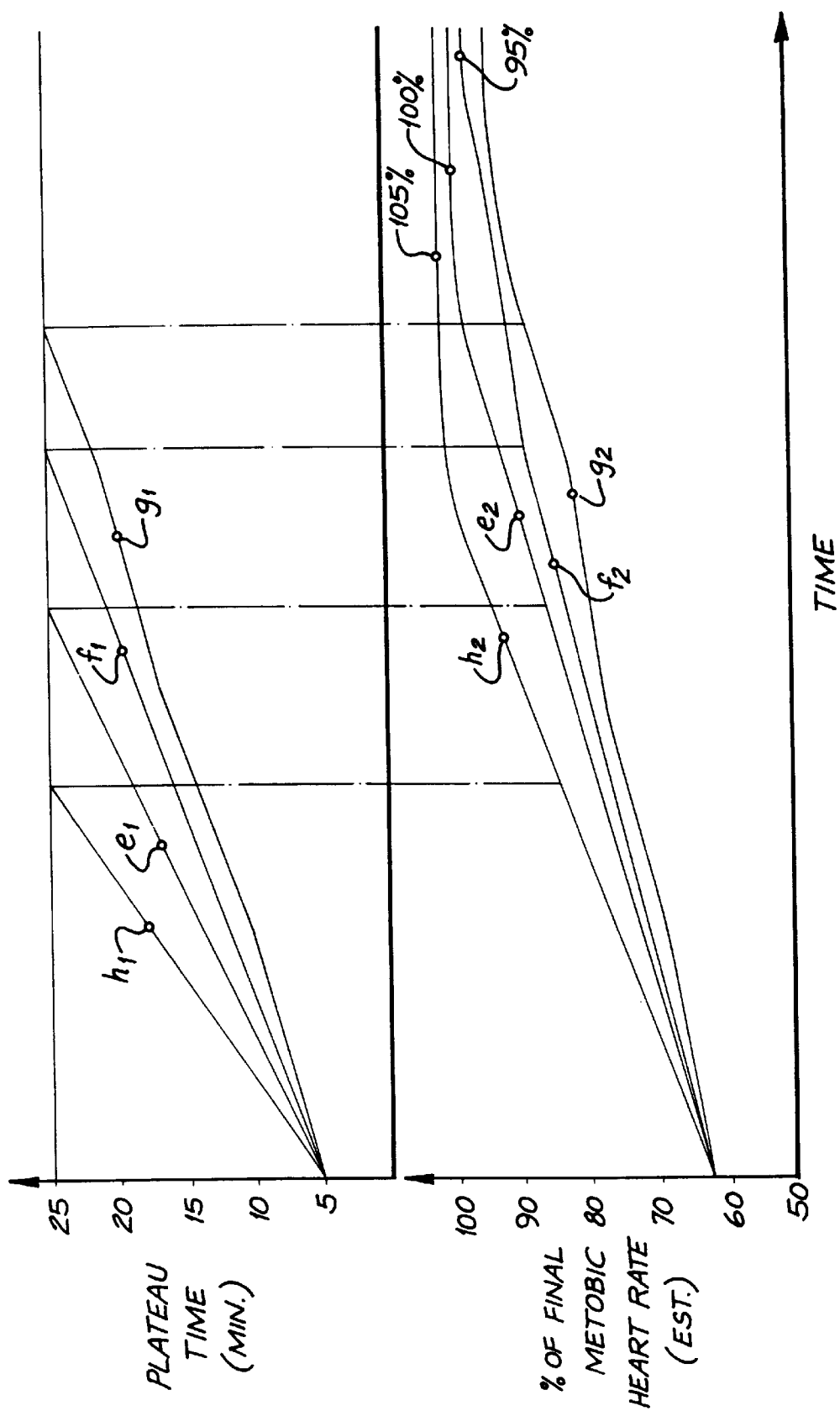
FIG. 6 graphically illustrates the effect of exercise prescription adjustment.

In FIG. 6, the upper curves show the length of time (in minutes) that the plateau portion of the exercise session lasts, as a function of the period over which the exercise program has run, while the bottom curve shows desired heart rate during the plateau period over the same period.

Referring to FIG. 6, if the curves marked (e) represent the prescription originally determined for the client then curves (f) might represent an adjusted prescription for a client finding the original prescription a little difficult, curves (g) might represent an adjusted prescription for a client who fails to maintain a regular exercise pattern and curves (h) might represent an adjusted prescription for a client who finds the original prescription too easy and therefore requires a slightly harder schedule.

During the maintenance phase the client will have passed the point in their prescription at which their heart rate during the plateau period is at least 90% of the estimated long term maximum metobic rate for the particular client and the plateau period has reached 25 minutes. At this point the plateau period will stop increasing and will remain at 25 minutes from there on.

The desired heart rate will continue to increase during the maintenance period, but only while the client is not over exerting. The heart rate is also restricted by an absolute maximum value for the particular client. In the event, that the original prescription was accurate, the heart rate will ramp up to the predicted long term metobic heart rate. However, in the event that the original prescription was not quite correct, the prescription will adjust itself toward a long term metobic heart rate band which is appropriate for the client and will approach that final heart rate band at a rate which is substantially optimised for the particular client. This heart rate band contains the actual long term metobic rate for the client as opposed to their estimated maximum metobic rate calculated at the commencement of the programme. In FIG. 6, curves (f) illustrate a prescription in which the client achieves a long term metobic heart rate which is about 95% of the estimated maximum metobic heart rate, while curves (h) illustrate a prescription in which the client achieves a long term metobic heart rate which is about 105% of the originally estimated maximum metobic rate.

In all of the curves of FIG. 6 it will be noted that the long term metobic heart rate is approached from below and the rate of change is relatively smooth with no significant discontinuities or abrupt changes. It will be appreciated that the curves of FIG. 6 are illustrative only and that in practice curves will have more undulation due to the adaptive nature of the system.

The present exercise monitoring system enables many users to be monitored by a single central computer. There is no restriction on location of where the user should exercise. It may only be infrequently necessary (or indeed not necessary at all) for the user to visit a central location in order to have his exercise programme set in the first place, and altered at infrequent intervals in accordance with his progress in the exercise regimen, and in order to re-examine pre-set physiological parameters for the user.

The master data processor 101 is arranged to automatically determine a suitable exercise regimen for a user on the basis of the physiological parameters for the user input to the master data processor. The master data processor will automatically perform appropriate calculations utilising the physiological data to produce a suitable initial exercise regimen for the particular user.

The physiological data can be obtained by the user attending a central location or by the user making the necessary measurements and completing a form provided with the user monitor, in which case the form would be forwarded to the central location and the data loaded into the computer which would then produce a string of data which when received by the user is entered by him into the monitor.

Alternatively the exercise monitor 102 may be programmed to accept user inputs of the required physiological data directly and to calculate the required beginning heart-print and initial rate of progression.

Based on the results of the physiological profile, an exercise programme will be designed with the following features:

1. It will require a "whole of body" physical activity of low intensity. Walking or swimming may be recommended.
2. The activity will take from 30 to 45 minutes each day to perform.
3. The user will be required to commit to performing the activity at least five out of every seven days without ever missing more than two days straight.

It will be appreciated that the system can be designed to produce any type of exercise programme. The exercise programme could be very different, for example if the person it is being designed for is very fit.

Figure 1:
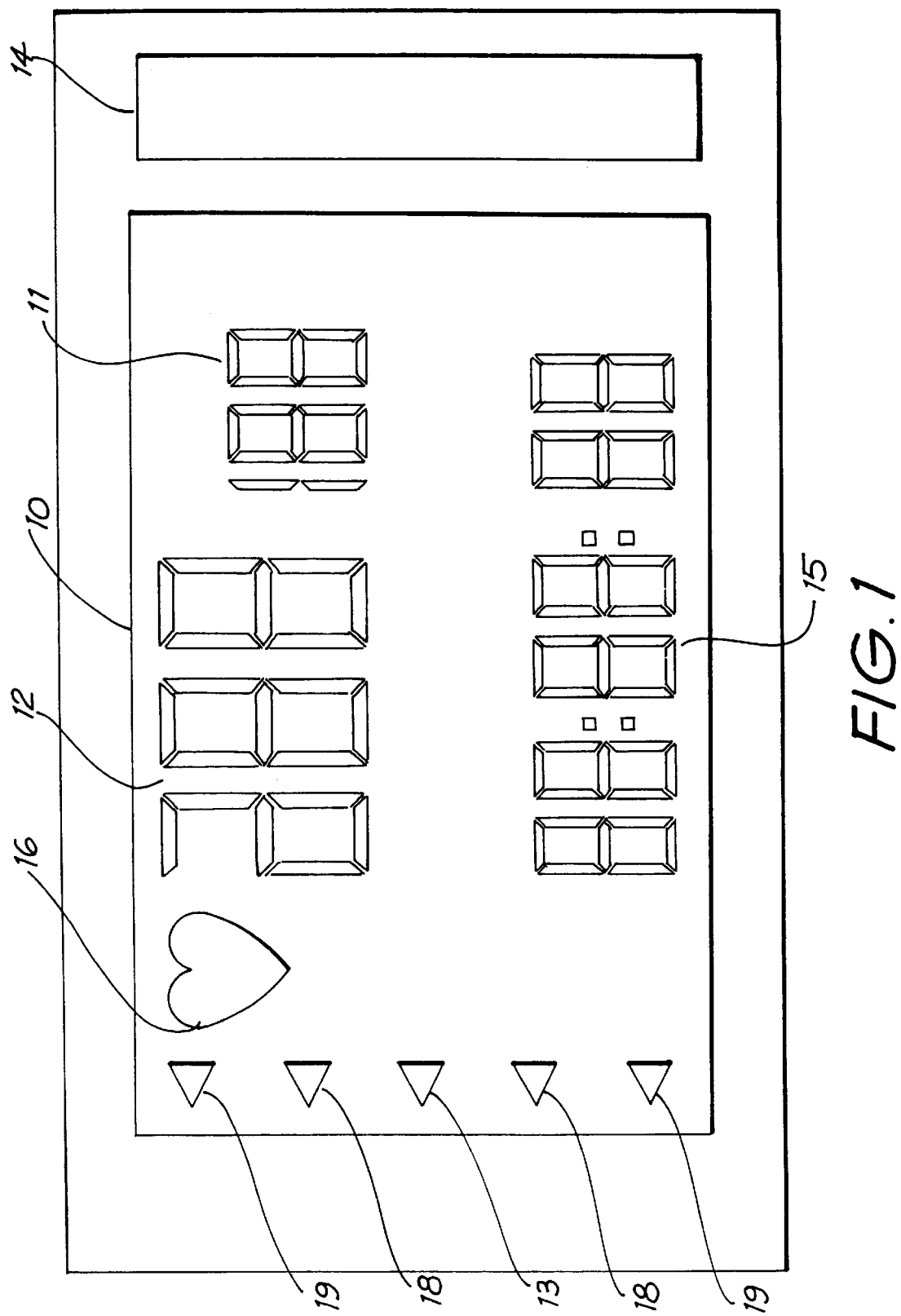
FIG. 1 is a front view of a user monitor in accordance with an embodiment of the present invention.
Figure 2:
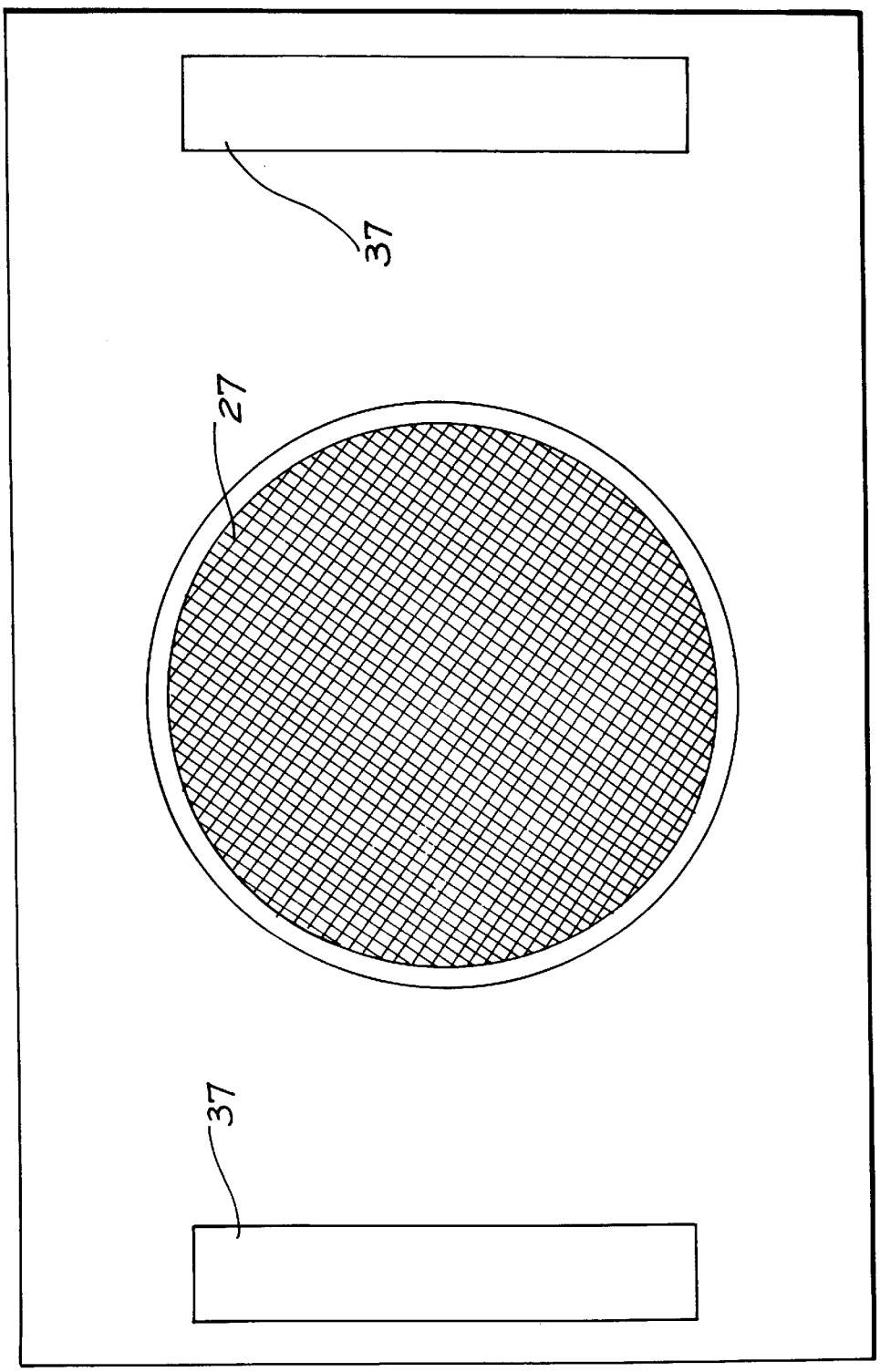
FIG. 2 is a rear view of the user monitor of FIG. 1A.
Figure 3:
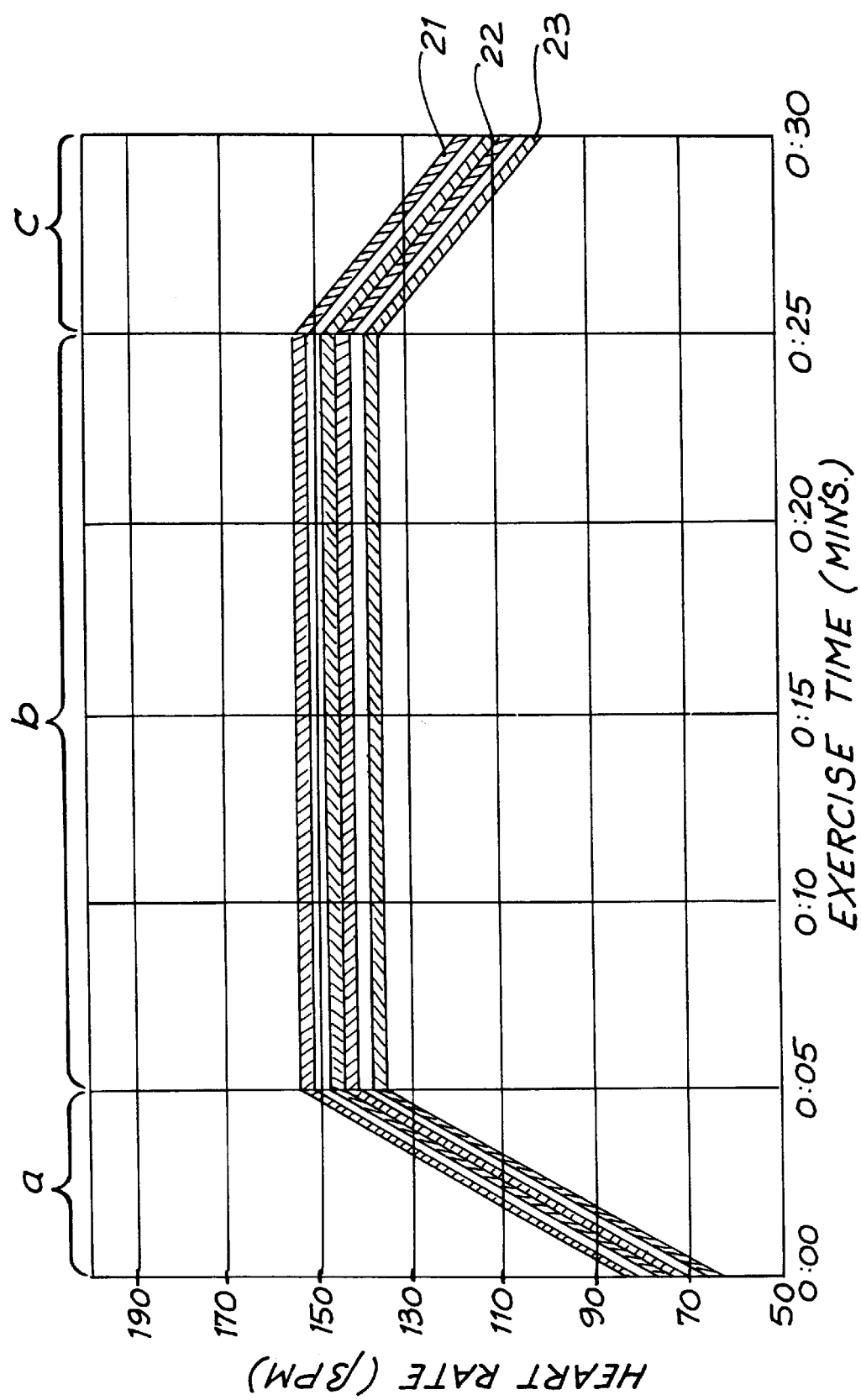
FIG. 3 is an illustration of a heart-rate curve for use in monitoring a user's progress in an exercise regimen, in accordance with an embodiment of the present invention.
Figure 4:
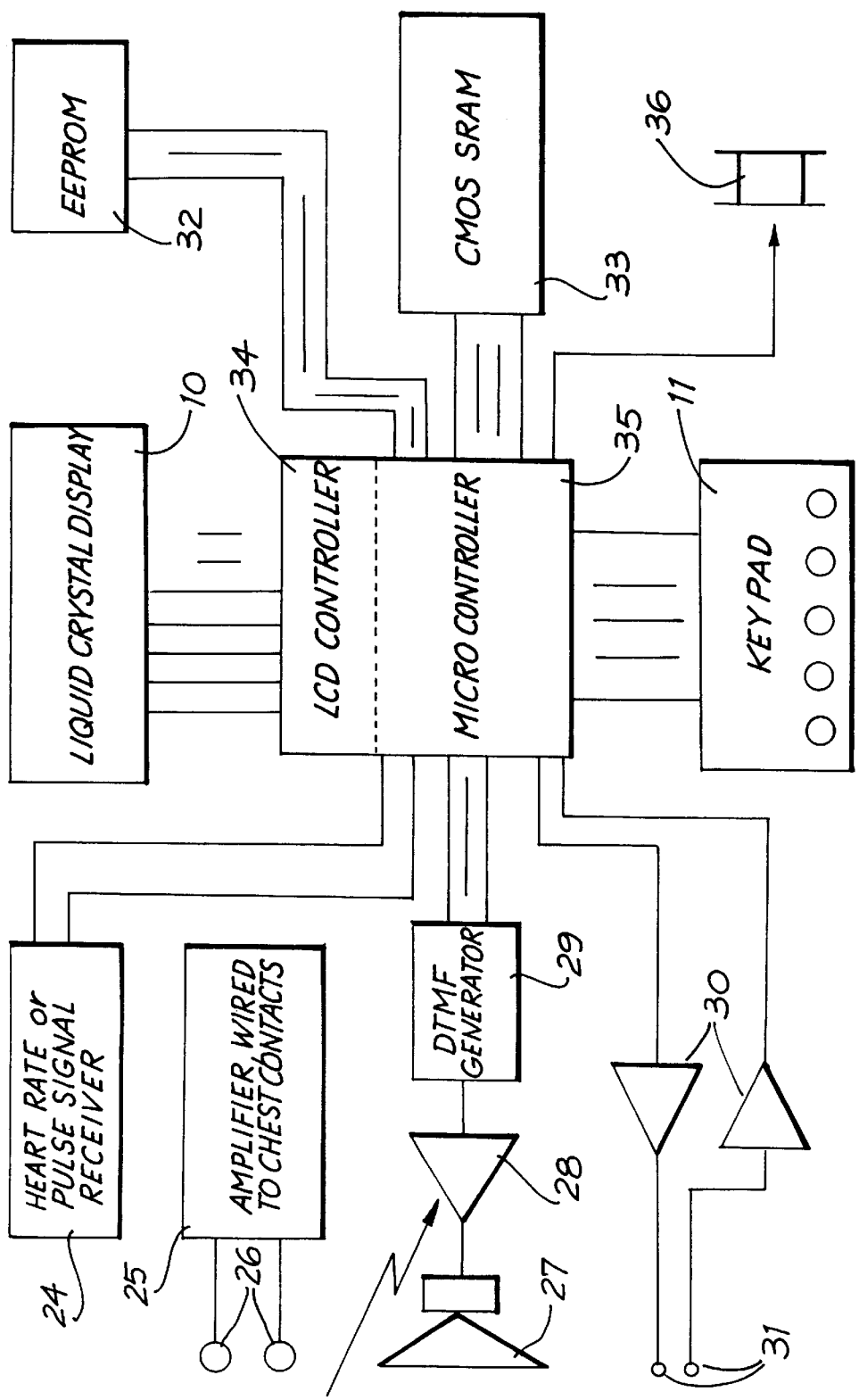
FIG. 4 is a schematic block circuit diagram of the user monitor of FIG. 1A and 1B.

The master data processor 101 or the heart monitor 102 will also produce a "heart-rate curve" (refer to FIG. 3) which is considered to be "ideal" for the exercise programme designed for the user. The heart-rate curve will be automatically produced by the master data processor 101 or the heart monitor 102 by the performance of suitable calculations using the physiological parameters and in consideration of the exercise programme which has been designed. As illustrated in FIG. 3, the heart-rate curve will consist of three sections:

Section a. This is the "warm up" zone following the commencement of exercise. In the preferred embodiment, this zone may last for five minutes.

Section b. This is the "exercise time" and will last for as long as required. For the average person it will be preferred that the regimen be designed so that the exercise is always aerobic.

Section c. This is the "cool down" zone and will always last five minutes, in the preferred embodiment.

The heart-rate curve illustrated in FIG. 3 includes three curves. The middle curve 22 is the user's ideal heart-rate curve for a particular exercise event. Curve 21 denotes an upper limit beyond which the user's heart-rate should not extend, and curve 23 a lower limit.

For every exercise event (every time the user performs a physical activity of his own choice) the user will be required to keep his heart-rate as close as possible to the ideal curve 22, and not go outside the limits denoted by curves 21 and 23. If the user sticks to this heart-rate curve, it is believed that he will obtain the maximum benefits from the exercise regimen. If he goes outside the curve, he may be over-exercising or under-exercising, thus not obtaining the full benefits of exercise.

In all cases in the preferred embodiment the three sections, a, b and c, of the heart-rate curve will be straight. This simplifies the extrapolations necessary from actual heart-rate data, to create the curve. Only two items of data need to be established in order to enable creation of a heart-rate curve for any user. These are the user's resting heart-rate (RHR) and the user's current metobic heart-rate (MBR). The RHR is the user's average heartbeat when he is at rest and not undergoing exercise. The MHR is the user's current ideal maximum heartbeat, calculated by the heart monitor 102, for period b, the actual exercise period after "warm up" and before "cool down". These items of data together with the current total exercise time calculated by the heart monitor 102 enable extrapolation to produce the heart-rate curve.

It is therefore not necessary for the heart monitor 102 or master data processor 101 to store a heart-rate curve in analogue form, as such. Instead, it need only store the items of data discussed above, from which the heart-rate curve can be created by extrapolation.

Printing means are associated with the master data processor 101 provided for printing out a heart-rate curve for the user.

The upper limit curve 21 and the lower limit curve 23 may be extrapolated from "threshold" values calculated from the physiological data input to the master data processor. Only two threshold values are required to enable determination of the upper and lower curves. These threshold values are, respectively, an upper limit on the heartbeat and a lower limit on the heartbeat. In the preferred embodiment the threshold values are calculated as a percentage of the current metobic heart-rate rounded to the nearest heart beat.

The user monitor 102, which is used by the user to monitor his progress and to determine whether or not he is following the heart-rate curve during exercise, will now be discussed in greater detail with reference to FIGS. 1 to 4.

Referring to the figures, the user monitor includes a display 10 for displaying information to assist the user, and for providing an indication to the user as to whether his heart-rate is above or below predetermined limits, an audible alarm 36 for a similar purpose, and control keypad 11 (not shown in detail). The user monitor also includes audio pulse generating means 27, 28, 29 for transmitting data down a telephone line to the master data processor.

The user monitor 102 is arranged to be mounted relative to the user in a convenient position to enable the user to exercise and view the display 10 at the same time. It is preferably mounted on the user's wrist. It should be noted that the size of the monitor as shown in the drawing is not the actual size. It is smaller than illustrated and of a convenient size to be mounted on a user's wrist.

The user monitor is operable in conjunction with a heartbeat monitor 25 which will be mounted on the user's chest proximate the heart. The heart monitor 25 includes two electrodes 26 for monitoring heartbeat and signal processing and transmission means (not illustrated) for transmitting a signal indicative of heart-rate to the user monitor 102. Such heart monitors are known. The user monitor 102 includes a receiver 24 and signal processing means 35 for processing the received signal to provide an indication of heart-rate. The transmission between the heart monitor and the user monitor may be by radio or induction.

Alternatively, the heart monitor can be dispensed with and the user monitor connected via amplifier not shown) to chest contacts 26 for detecting the heart beat.

The user monitor also includes memory means 32 for storing data relating to the ideal heart-rate curve previously determined, i.e. RHR and MHR and exercise time. The processor means 35 also provides "reconstruction" of the ideal heart-rate curve from this stored data. Threshold data will also be stored in the user monitor to enable a determination of upper and lower limits for heart-rate during an exercise period.

RAM 33 is used to store data sampled during the performance of an exercise event.

In operation, during the performance of an exercise event, the processor means 35 of the user monitor makes an ongoing comparison during the time of the exercise event of the user's heart-rate with the heart-rate curve reconstructed from the heart-rate data currently held in the user monitor. A display 12 of the user's actual heart-rate is provided and display 11 of the required heart-rate in order for the user to follow the heart-rate curve at that particular time. Further visual and audio indicators are given for indicating whether the user is within the predetermined limits of the ideal heart-rate curve. These include threshold indicators 13, 18 and 19, which provide an indication whether the user's heartbeat is over or under the ideal heart-rate curve. Audible alarms are also given via a piezo element 36 to indicate whether the user's heartbeat is too high (high-pitched warning) or too low (low-pitched warning).

The processor means 35 of the user monitor is able to calculate, from the data stored therein, the heart-rate curve required as the exercise event is performed as well as threshold levels outside which the heart-rate of the user should not be extending at any particular time during the exercise event (as a percentage of the current metobic rate for example). More than one threshold value, above and below the current nominal heart-rate curve, is given.

For example, a "yellow" signal 18 on threshold indicators may indicate plus or minus six heartbeats from the ideal heart-rate curve, while a "red" indication 19 may indicate plus or minus 9 heartbeats. The alarm may sound at yet another threshold, if desired, for example the threshold value determined by curves 21 and 23 of FIG. 3.

The heart-rate curve can easily be extrapolated from knowledge of the resting heart-rate and current metobic heart rate and exercise time held in the heart rate monitor 102, and adaptively updated after each exercise session.

User feedback of the Borg rating previously discussed is entered into the monitor 102 via a keypad 14, enabling automatic adjustment of the prescription to follow the client's progress.

A timer display 15 is also provided which enables the user to monitor the time of exercise. This timer may be set to count three time intervals, being the warm-up period, the exercise period and the cool-down period.

A further display arranged to indicate the relative heart-rate is a display element 16 in the shape of a heart arranged to pulse on and off to indicate the user's heart-rate during exercise.

The user monitor contains a memory 33 arranged to store data relating to the performance of a user exercise event. The heart-rate of the user during an exercise event will be sampled at predetermined time periods by the user monitor and stored in the memory for subsequent downloading to the master data processing means 101 by way of the pulse code generator 29, 28, 27. The user monitor is also provided with an optical port or wired interface 30 which enables communication with a PC or master data processor means for programming or downloading of data.

An advantage of an optical port is that it electrically isolates the user monitor from the device it is communicating with. The optical port also potentially enables the heart beat to be monitored by way of an infrared connection to a transmitter located approximate the heart. It may also enable output to a visual display unit, such as a television display, to enable a magnified display of heart rate, etc to be provided for the user.

The user monitor thus provides a convenient means by which the user may monitor his heart-rate and performance during the carrying out of an exercise event. The back of the user monitor is provided with a covering of Velcro or the like 37. This enables the user monitor to be adhered to a wristband, to a surface of an exercise machine (for example an exercise bicycle, jogger, or step-up machine), or to any appropriate surface where the monitor can be conveniently viewed by the user.

The user will be expected to download data relating to his performance during his exercise regimen to the master data processor, by way of the pulse code output 27. All the user has to do is telephone the interactive voice response computer 105, hold the pulse code output 27 against the telephone and actuate an appropriate push button on the keyboard 4 in order to transfer data relating to an exercise event to the master data processor 101 which receives the data over a network from the interactive voice response computer 105. The user monitor 102 may store information for only one exercise event. This prompts the user to download the data to the master data processor means 101. He will not be able to use the user monitor 102 to perform a subsequent exercise event until he has done this. The user monitor 102 will appropriately "tag" information for a particular exercise event, so that it may be identified in time and also by user ID. Conveniently, each user monitor 102 will be provided with an ID known to the master data processor 101. The master data processor 101 will then be able to compare the data for each exercise event with the ideal heart-rate curve 22 and assess the user's performance.

The master data processor 101, as well as monitoring and comparing data from the user monitor 102, will also store the user information relating to his physiological profile, produce the heart-rate data curve which is ideal for the user, produce regular reports for the user, etc.

In the described embodiment, the heart rate curve has been used as a tool for monitoring the user's progress. It is possible that other physical parameters could be monitored than heart-rate. The present invention is not limited to a system which monitors the user's progress by monitoring heart rate.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

I claim:

1. An exercise monitor for monitoring the progress of a user in an exercise regime, said exercise monitor comprising:

a monitor for measuring physical parameter data pertaining to the user during an exercise event;

a first memory device for storing preset physical parameter values;

a controller for receiving and comparing the preset physical parameter values with the measured physical parameter data;

an indicator connected to said controller for signifying to the user a required change in exercise intensity when the measured physical parameter data differs from the preset physical parameter values stored in said first memory device by an amount greater than a predetermined allowable tolerance; and an input device connected to said controller for inputting data indicative of degree of difficulty experienced by the user while completing an exercise session within the allowable tolerance of the preset values, said controller altering the preset values in said first memory device in response to the data input entered by the user using said input device.

2. An exercise monitor in accordance with claim 1, wherein said indicator displays a preferred effort rating at the end of each exercise event.

3. An exercise monitor in accordance with claim 2, wherein said input device is used to change the rating based on the user's perception of the degree of difficulty experienced during the exercise event.

4. An exercise monitor in accordance with claim 3, said input device having a face, wherein said input device comprises buttons on the face of said monitor for adjustment of the rating.

5. An exercise monitor in accordance with claim 3, wherein the effort rating has an optimum value of approximately 12.

6. An exercise monitor in accordance with claim 3, wherein the effort rating value increases as an amount of effort expended by the user increases.

7. An exercise monitor in accordance with claim 3, wherein said controller automatically alters a prescription based on a pattern of effort rating values over a predetermined period of time.

8. An exercise monitor in accordance with claim 1, wherein the physical parameter is a measure of heart-rate over a period of time during exercise.

9. An exercise monitor in accordance with claim 1, wherein said indicator displays the physical parameter while the user is exercising.

10. An exercise monitor in accordance with claim 1, further comprising a second memory device for monitoring and storing the measured physical parameter value relating to the user exercise event.

11. An exercise monitor in accordance with claim 10, wherein the stored physical parameter values relate to the heart-rate of the user.

12. An exercise monitor in accordance with claim 11, wherein said monitor comprises a heart monitor for measuring the heart-rate of the user at time intervals during the exercise event, and said memory device stores the heart-rate data measured by said heart monitor.

13. An exercise monitor in accordance with claim 11, wherein said memory device stores physical parameter data other than a measured heart-rate.

14. An exercise monitor in accordance with claim 10, wherein the stored physical parameter values are provided as a heart-rate curve comprising a set of coordinates of heart-rate versus time during a period of a single exercise event.

15. An exercise monitor in accordance with claim 10, wherein said second memory device stores data defining a heart-rate curve specific to a particular user and calculated based on measured parameters associated with the user's physical condition.

16. An exercise monitor in accordance with claim 10, wherein said second memory device generates a heart-rate curve based on stored heart-rate data, and said controller compares the heart-rate of the user during the exercise event with the generated heart-rate curve, to determine whether the user's heart-rate is within predetermined acceptable limits of the heart-rate curve.

17. An exercise monitor in accordance with claim 16, wherein the heart-rate curve is stored as a plurality of heart-rate readings for predetermined time intervals during the exercise event.

18. An exercise monitor in accordance with claim 17, wherein the heart rate curve is extrapolated based on the stored data.

19. An exercise monitor in accordance with claim 8, wherein said first memory device stores date and time information regarding the exercise event.

20. An exercise monitor in accordance with claim 19, wherein the date and time information is associated with the physical parameter values for the particular exercise event.

21. An exercise monitor in accordance with claim 8, further comprising:

a master data processor; and a communication device for transmitting at the user's convenience the stored physical parameter value to said master data processor.

22. An exercise monitor in accordance with claim 21, wherein said first memory device stores preset values corresponding to values stored in said master data processor for the physical parameter.

23. An exercise monitor in accordance with claim 21, further comprising means for downloading the stored data relating to an exercise event to said master data processor.

24. An exercise monitor in accordance with claim 23, wherein said downloading means comprises means for interfacing with a standard telephone set to transmit information via a telephone line to said master data processor.

25. An exercise monitor in accordance with claim 21, wherein said monitor gathers time and date information by tracking the time from an exercise event to the point when that event is reported to said master data processor.

26. An exercise monitor in accordance with claim 1, wherein said monitor stores data identifying the user.

27. An exercise monitor in accordance with claim 1, wherein said monitor is switchable to a logging mode for recording a physical parameter over a logging period.

28. An exercise monitor in accordance with claim 27, said monitor is switchable to a login mode for recording a physical parameter over a logging period at regular intervals the period of which varies over the length of the logging period.

* * * * *

UNITED STATES PATENT AND TRADEMARK OFFICE
CERTIFICATE OF CORRECTION

PATENT NO. : 5,921,891
DATED      : July 13, 1999
INVENTOR(S) : Neville James BROWNE It is certified that error appears in the above-identified patent and that said Letters Patent is hereby corrected as shown below:

On the title page, item:

[75] Inventor, "JAMES NEVILLE BROWNE" should be --NEVILLE JAMES BROWNE--.

Signed and Sealed this

Twenty-fifth Day of January, 2000

Attest:

Attesting Officer

Acting Commissioner of Patents and Trademarks